US009481618B2

(12) United States Patent
Itami et al.

(10) Patent No.: US 9,481,618 B2
(45) Date of Patent: Nov. 1, 2016

(54) CYCLOPOLYARYLENE COMPOUND AND METHOD OF MANUFACTURING SAME

(75) Inventors: Kenichiro Itami, Nagoya (JP); Yasutomo Segawa, Nagoya (JP); Akiko Yagi, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 306 days.

(21) Appl. No.: 14/003,512

(22) PCT Filed: Mar. 9, 2012

(86) PCT No.: PCT/JP2012/056116
§ 371 (c)(1),
(2), (4) Date: Nov. 15, 2013

(87) PCT Pub. No.: WO2012/121370
PCT Pub. Date: Sep. 13, 2012

(65) Prior Publication Data
US 2014/0066661 A1 Mar. 6, 2014

(30) Foreign Application Priority Data

Mar. 9, 2011 (JP) ................................. 2011-052045

(51) Int. Cl.
| | |
|---|---|
| C07C 15/20 | (2006.01) |
| C07C 1/28 | (2006.01) |
| C07C 41/30 | (2006.01) |
| C07C 43/188 | (2006.01) |
| C07C 1/22 | (2006.01) |
| C07C 2/64 | (2006.01) |
| C07C 39/12 | (2006.01) |
| C07C 43/20 | (2006.01) |
| C07C 35/52 | (2006.01) |
| C07C 43/192 | (2006.01) |

(52) U.S. Cl.
CPC .................. *C07C 15/20* (2013.01); *C07C 1/22* (2013.01); *C07C 1/28* (2013.01); *C07C 2/64* (2013.01); *C07C 35/52* (2013.01); *C07C 39/12* (2013.01); *C07C 41/30* (2013.01); *C07C 43/188* (2013.01); *C07C 43/192* (2013.01); *C07C 43/20* (2013.01); *C07C 2101/16* (2013.01); *C07C 2102/10* (2013.01); *C07C 2103/90* (2013.01)

(58) Field of Classification Search
CPC ................ C07C 39/12; C07C 15/20
See application file for complete search history.

(56) References Cited

FOREIGN PATENT DOCUMENTS

JP 2010-168363 A 8/2010

OTHER PUBLICATIONS

Yagi et al, Journal of the American Chemical Society, Synthesis and Properties of [9]Cyclo-1,4-naphthylene: A π-Extended Carbon Nanoring, 2012, 134, pp. 2962-2965.*
Akiko Yagi et al., "Synthesis and Properties of [9]Cyclo-1,4-naphthylene: a π-Extended Carbon Nanoring," Journal of the American Chemical Society, Feb. 15, 2012, vol. 134, No. 6, pp. 2962-2965.
Ramesh Jasti et al., "Synthesis, Characterization, and Theory of [9]-, [12]-, and [18]Cycloparaphenylene: Carbon Nanohoop Structures," Journal of the American Chemical Society, 2008, vol. 130, No. 52, pp. 17646-17647.
Hiroko Takaba et al., "Selective Synthesis of [12]Cycloparaphenylene," Angewandte Chemie International Edition, 2009, vol. 48, pp. 6112-6116.
Haruka Omachi et al., "A Modular and Size-Selective Synthesis of [n]Cycloparaphenylenes: A Step toward the Selective Synthesis of [n,n] Single-Walled Carbon Nanotubes," Angewandte Chemie International Edition, 2010, vol. 49, pp. 10202-10205.
Shigeru Yamago et al., "Synthesis of [8]Cycloparaphenylene from a Square-Shaped Tetranuclear Platinum Complex," Angewandte Chemie International Edition, 2010, vol. 49, pp. 757-759.
International Search Report dated Jun. 5, 2012 issued for PCT/JP2012/056116.

* cited by examiner

*Primary Examiner* — Paul A Zucker
(74) *Attorney, Agent, or Firm* — Locke Lord LLP; James E. Armstrong, IV; Nicholas J. DiCeglie, Jr.

(57) ABSTRACT

A cyclopolyarylene compound represented by Formula (1):

(1)

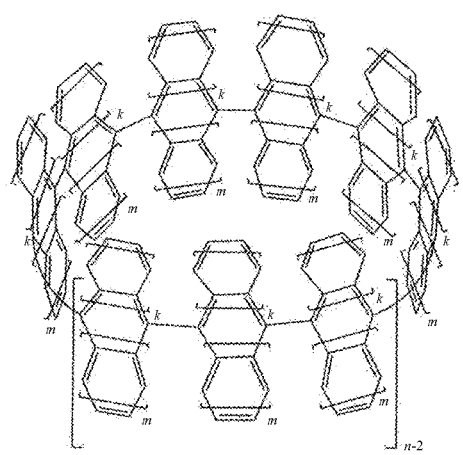

wherein k is the same or different, and each represents 0, 1 or 2; m is the same or different, and each represents 1, 2 or 3; and n represents 3, 4, 5 or 6.

5 Claims, 1 Drawing Sheet

[n] cycloparaphenylene ([n] CPP)

CYCLOPOLYARYLENE COMPOUND AND METHOD OF MANUFACTURING SAME

TECHNICAL FIELD

The present invention relates to a cyclopolyarylene compound and a production method thereof.

BACKGROUND ART

Hitherto-known nanostructures containing carbon atoms include carbon nanotubes made of a cylindrically rolled two-dimensional graphene sheet.

Carbon nanotubes have high electrical conductivity, high mechanical strength, superior elasticity, heat resistance, and are lightweight. With these advantageous properties, carbon nanotubes are expected to be applied to various fields, including chemistry, electronics, and life science.

Carbon nanotubes can be produced through arc discharge, laser furnaces, chemical vapor deposition, and the like. However, these methods have a disadvantage in that they can only produce mixtures of carbon nanotubes of various lengths and diameters.

Recent studies reported research on a cycloparaphenylene compound, which is the smallest unit for making a carbon nanotube. FIG. 1 shows an example of a structure of a cycloparaphenylene compound.

For example, Non-Patent Document 1 discloses a method for producing a cycloparaphenylene compound as a mixture having a cyclic structure composed of 9, 12, or 18 continuously bonded benzene rings, using 1,4-diiodobenzene and benzoquinone as materials.

Non-Patent Documents 2 and 3 disclose a method for producing a cycloparaphenylene compound having a cyclic structure in which 12 benzene rings are regularly bonded, using 1,4-cyclohexanedione and 1,4-diiodobenzene.

Non-Patent Document 4 discloses a method for producing a cycloparaphenylene compound in which 8 benzene rings are regularly bonded through reductive elimination of a square-shaped biphenylene platinum complex with bromine.

The cycloparaphenylene compounds disclosed in the above Non-Patent Documents have a cyclic chemical structure in which multiple phenylene groups are singly bonded. This structure has an interesting property as the smallest unit for making an armchair single-walled carbon nanotube.

CITATION LIST

Non-Patent Documents

Non-Patent Document 1: Jasti, R. et al., J. Am. Chem. Soc., 2008, 130, 17646
Non-Patent Document 2: Itami, K. et al., Angew. Chem. Int. Ed., 2009, 48, 6112
Non-Patent Document 3: Itami, K. et al., Angew. Chem. Int. Ed., 2010, 49, 10202
Non-Patent Document 4: Yamago, S. et al., Angew. Chem. Int. Ed., 2010, 49, 757

SUMMARY OF INVENTION

Technical Problem

The inventors of the present invention assumed that a compound (hereinafter may be referred to as a "cyclopolyarylene compound") obtained by converting the phenylene groups, which are constitutional units of the ring of the aforementioned cycloparaphenylene compound, into bivalent condensed polycyclic aromatic hydrocarbon groups also has an interesting characteristic derived from the distinctive structure, as well as the aforementioned cycloparaphenylene compound.

Accordingly, an object of the present invention is to provide a cyclopolyarylene compound and a production method thereof.

Solution to Problem

The inventors of the present invention conducted extensive research to solve the above problems, and found that the target compound can be easily synthesized in several steps using a readily available specific material. The inventors conducted further research based on such a finding, and completed the present invention.

Specifically, the present invention encompasses the following cyclopolyarylene compounds or precursors thereof, and their production methods.

Item 1. A cyclopolyarylene compound represented by Formula (1):

[Chem. 1]

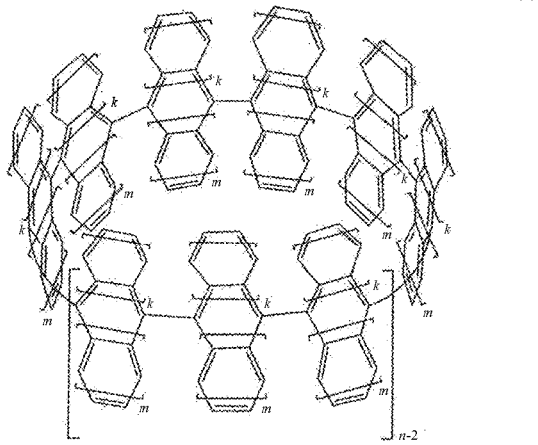

(1)

wherein k is the same or different, and each represents 0, 1 or 2; m is the same or different, and each represents 1, 2 or 3; and n represents 3, 4, 5 or 6.

Item 2. The cyclopolyarylene compound according to Item 1, wherein all k are the same; and all m are the same in Formula (1).

Item 3. The cyclopolyarylene compound according to Item 1 or 2, wherein all k are 0 or 1; all m are 1 or 2; and n is 3 or 4 in Formula (1).

Item 4. A compound represented by Formula (2):

[Chem. 2]

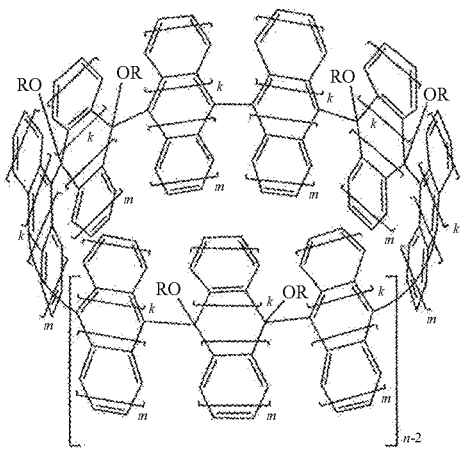

(2)

wherein R is the same or different, and each represents hydrogen atom, alkyl group or protecting group for hydroxy group; k is the same or different, and each represents 0, 1 or 2; m is the same or different, and each represents 1, 2 or 3; and n represents 3, 4, 5 or 6.

Item 5. The compound according to Item 4, wherein all R are the same; all k are the same; and all m are the same in Formula (2).

Item 6. A method for producing a cyclopolyarylene compound represented by Formula (1):

[Chem. 3]

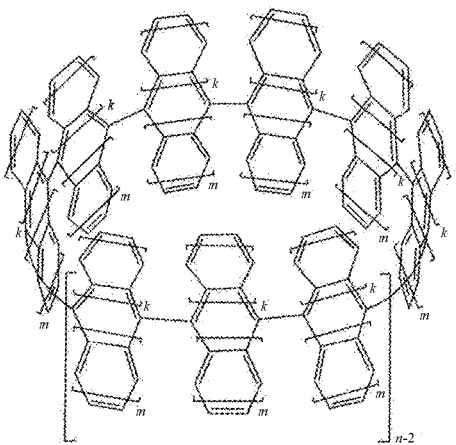

(1)

wherein k is the same or different, and each represents 0, 1 or 2; m is the same or different, and each represents 1, 2 or 3; and n represents 3, 4, 5 or 6, the method comprising the step of aromatizing a compound represented by Formula (2):

[Chem. 4]

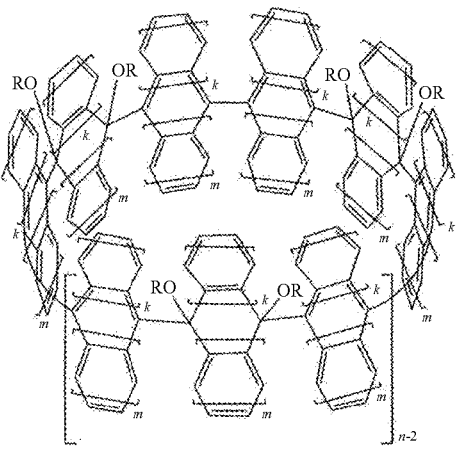

(2)

wherein R is the same or different, and each represents hydrogen atom, alkyl group or protecting group for hydroxy group; and k, m and n are as defined above.

Item 7. The method according to Item 6, comprising the step of reacting a compound represented by Formula (3):

[Chem. 5]

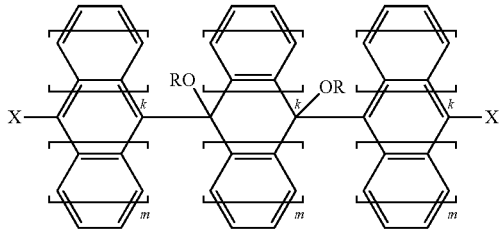

(3)

wherein X is the same or different, and each represents halogen atom; and R, k and m are as defined above, in the presence of a transition metal compound, thereby obtaining the compound represented by Formula (2).

Item 8. A method for producing a compound represented by Formula (2):

[Chem. 6]

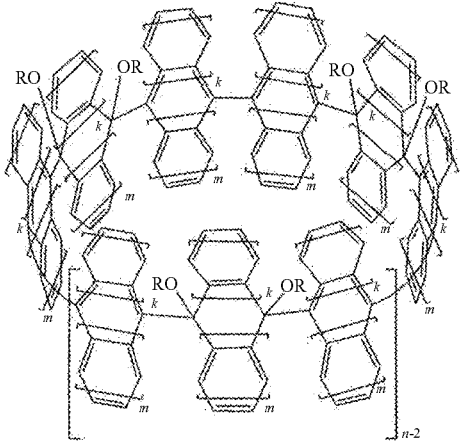

(2)

wherein R is the same or different, and each represents hydrogen atom, alkyl group or protecting group for hydroxy group; k is the same or different, and each represents 0, 1 or 2; m is the same or different, and each represents 1, 2 or 3; and n represents 3, 4, 5 or 6, the method comprising the step of reacting a compound represented by Formula (3):

[Chem. 7]

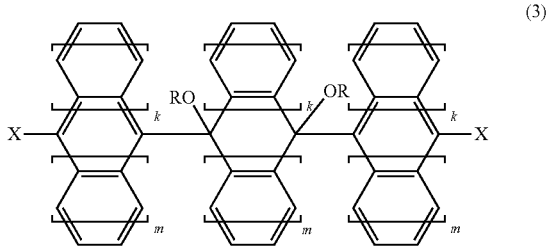

(3)

wherein X is the same or different, and each represents halogen atom; and R, k and m are as defined above, in the presence of a transition metal compound.

Item 9. A compound represented by Formula (3):

[Chem. 8]

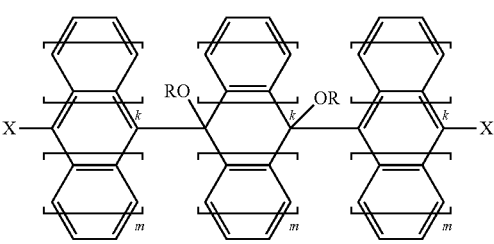

(3)

wherein X is the same or different, and each represents halogen atom; R is the same or different, and each represents hydrogen atom, alkyl group or protecting group for hydroxy group; k is the same or different, and each represents 0, 1 or 2; and m is the same or different, and each represents 1, 2 or 3.

Effects of Invention

The production method of the present invention enables production of the cyclopolyarylene compound represented by Formula (1) with a short production process at a high yield using a readily available compound as a starting material.

First, the compound represented by Formula (3a) is obtained from a readily available compound represented by Formula (4) and a compound represented by Formula (5). The compound represented by Formula (3a) can be selectively produced to have a cis configuration. Accordingly, the compound has a curved L-shape.

Next, the compound represented by Formula (3a) is converted into a compound represented by Formula (3b) by alkylating or protecting a hydroxyl group, and resulting Compound (3b) is cyclized by reaction (homocoupling reaction) in the presence of a transition metal compound, thereby obtaining a cyclic compound represented by Formula (2) corresponding to a trimer, tetramer, pentamer, or hexamer of the compound. Since the above cyclic compound represented by Formula (3b) used as a raw material has an L-shape, the cyclization reaction is efficiently advanced.

Finally, a compound represented by Formula (2) is subjected to reductive aromatization reaction, thereby obtaining the cyclopolyarylene compound represented by Formula (1).

The resulting cyclopolyarylene compound represented by Formula (1) is a novel compound, which has high solubility to organic solvents, a narrow HOMO-LOMO gap, and the like, compared with the cycloparaphenylene compounds disclosed in Non-Patent Documents 1 to 4. Accordingly, the compound is suitable for electronic materials, luminescence materials, and the like.

Further, the cyclopolyarylene compound represented by Formula (1) is assumed to be useful as a stable template or scaffold for selective synthesis of a carbon nanotube (CNT) having a uniform diameter.

DESCRIPTION OF EMBODIMENTS

Figure 1:
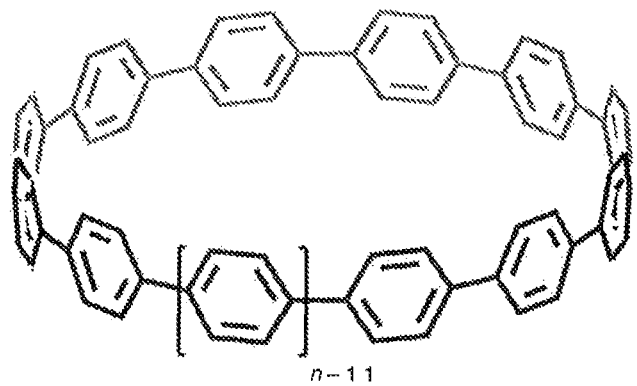
FIG. 1 shows an example of a [n]cycloparaphenylene compound. n is a number of phenylene groups.

The cyclopolyarylene compound of the present invention represented by Formula (1):

[Chem. 9]

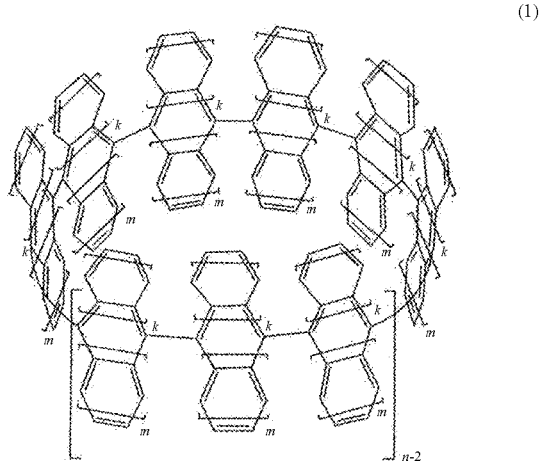

(1)

wherein k is the same or different, and each represents 0, 1 or 2: m is the same or different, and each represents 1, 2 or 3; and n represents 3, 4, 5 or 6, is a cyclopolyarylene compound having a cyclic structure in which repeating units (each unit is represented by Formula (6):

[Chem. 10]

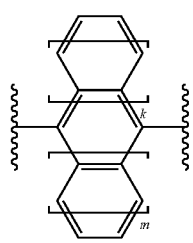
(6)

wherein k and m are as defined above) are continuously bonded. The compound represented by Formula (1) of the present invention may be a compound having only one type of repeating unit represented by Formula (6), or multiple different repeating units each satisfying Formula (6).

In Formula (1), k is the same or different, and each represents 0, 1 or 2. k may be the same or different, but is preferably the same. k is preferably 0 or 1. In Formula (1), m is the same or different, and each represents 1, 2 or 3. m may be the same or different, but is preferably the same. Further, m is preferably 1 or 2, more preferably 1. More specifically, the condensed polycyclic aromatic hydrocarbon moiety in Formula (6) is preferably constituted of naphthalene, anthracene, naphthacene, pentacene, or the like. Naphthalene and anthracene are particularly preferable.

In Formula (1), n is 3, 4, 5 or 6, preferably 3, 4 or 5, more preferably 3 or 4, particularly preferably 3. More specifically, the number of the repeating units represented by Formula (6) in the compound is 9, 12 or 15, more preferably 9 or 12, particularly preferably 9.

More preferable example is the following Compound (1a) in which all k are 0, all m are 1, and n is 3.

[Chem. 11]

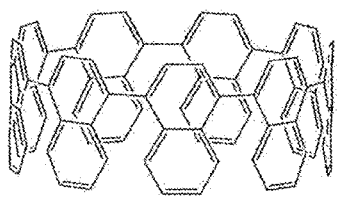
(1a)

Other more preferable examples include the following Compound (1b) in which all k are 1, all m are 1, n is 3, and Compound (1c) in which all k are 0, all m are 2, and n is 3.

[Chem. 12]

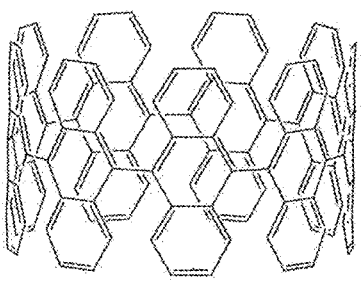
(1b)

[Chem. 13]

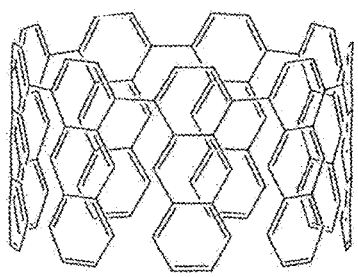
(1c)

The cyclopolyarylene compound represented by Formula (1) of the present invention can be produced by, for example, a method represented by Reaction Formula 1.

Reaction Formula 1

[Chem. 14]

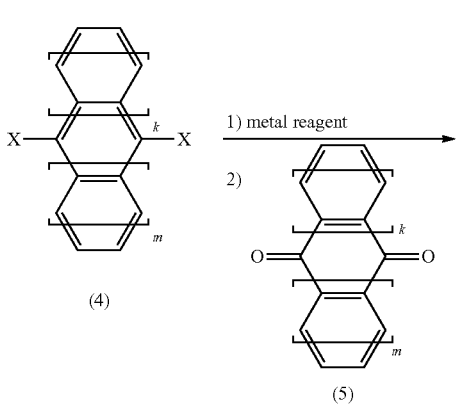

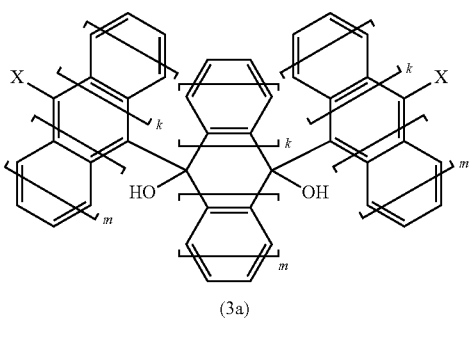

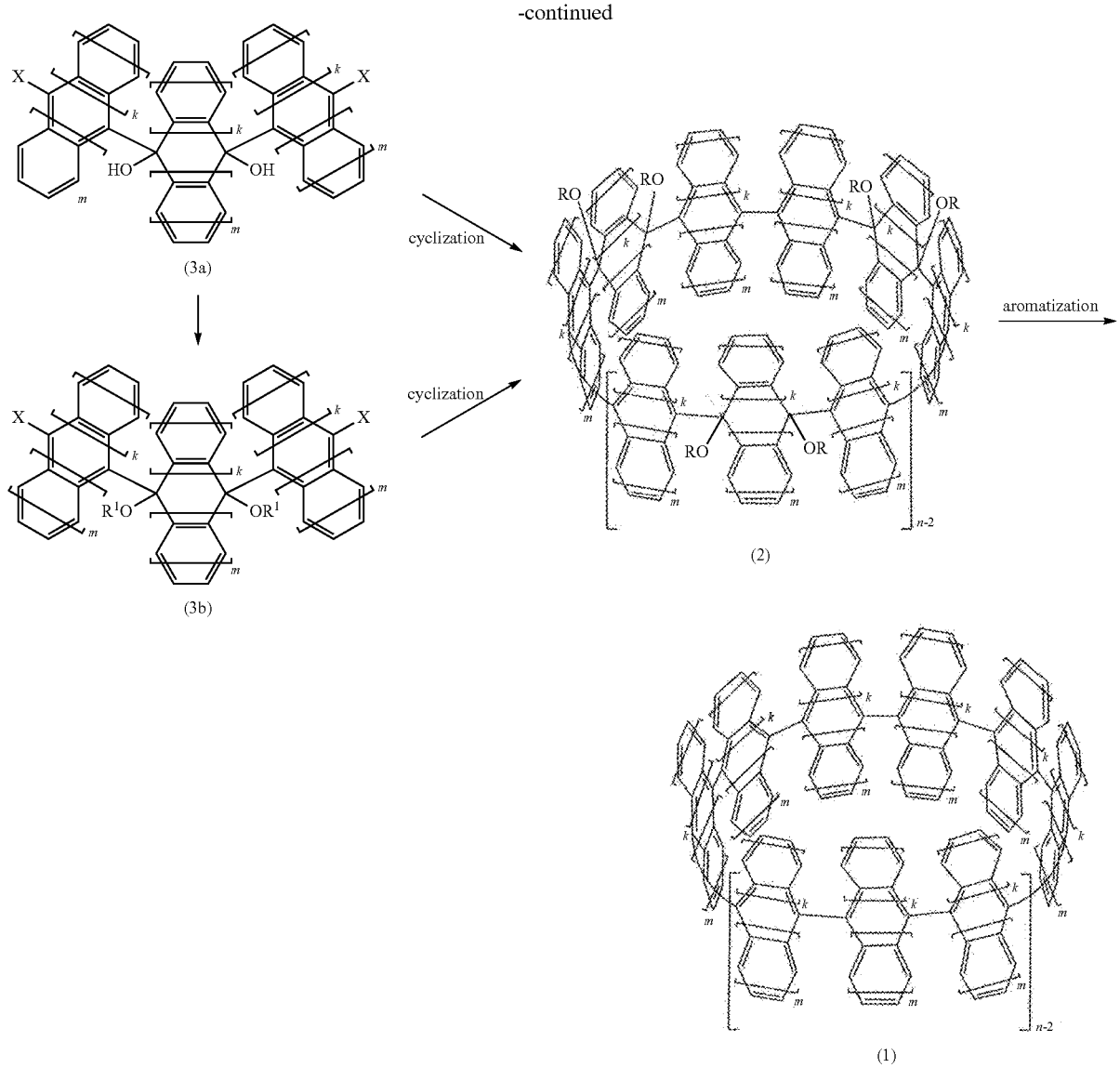

wherein X is the same or different, and each represents halogen atom; $R^1$ is the same or different, and each represents alkyl group or protecting group for hydroxy group; R is the same or different, and each represents hydrogen atom, alkyl group or protecting group for hydroxy group; and k, m and n are as defined above.

Examples of the halogen atom represented by X include fluorine atom, chlorine atom, bromine atom, and iodine atom. Bromine atom and iodine atom are preferable. X may be the same or different, but is preferably the same.

Examples of alkyl group represented by $R^1$ include $C_{1-6}$ alkyl groups, preferably $C_{1-3}$ alkyl groups, more preferably a methyl group or an ethyl group, particularly preferably a methyl group. The alkyl group having a carbon number of 3 or more may be a linear or branched-chain alkyl group.

Examples of the protecting group for hydroxy group represented by $R^1$ include alkanoyl group (e.g., $C_{1-4}$ alkanoyl group such as formyl group, acetyl group, or propionyl group), substituted or unsubstituted aralkyl group (e.g., benzyl group, p-methoxy-benzyl group, or p-nitrobenzyl group), silyl group (e.g., trimethylsilyl group, triethylsilyl group, or t-butyl dimethyl silyl group), alkoxy alkyl group (e.g., methoxymethyl group), and tetrahydropyranyl (THP) group.

Among them, $R^1$ is preferably an alkyl group, particularly preferably a methyl group.

$R^1$ and hydrogen atom (H) may be collectively referred to as R. As with $R^1$, this R is preferably an alkyl group, particularly preferably a methyl group.

Synthesis of Compound (3a)

The compound represented by Formula (3a) may be produced by converting one of the halogen atoms (X) in the compound represented by Formula (4) using a metal reagent (First Step; halogen-metal exchange reaction), and reacting the resulting compound and the compound represented by Formula (5) (Second Step).

Examples of the compound represented by Formula (4) include 1,4-dihalonaphthalene, 1,4-dihaloanthracene, 9,10-dihaloanthracene, 1,4-dihalonaphthacene, and 5,12-dihalonaphthacene; more specifically, 1,4-dibromo-naphthalene, 1,4-diiodonaphthalene, 1-bromo-4-iodonaphthalene, 1,4-dibromo-anthracene, 1,4-diiodoanthracene, 1-bromo-4-iodoanthracene, 9,10-dibromoanthracene, 9,10-diiodoanthracene, 9-bromo-10-iodoanthracene, and the like.

Examples of the compound represented by Formula (5) include 1,4-naphthoquinone, 1,4-anthracenedione, 9,10-anthracenedione, 1,4-naphthacenedione, and 5,12-naphthacenedione.

The reaction is generally performed in the presence of a solvent. In both the First and Second Steps, for example, ethers such as diethylether, diisopropyl ether, tetrahydrofuran (THF), 1,4-dioxane, dimethoxyethane (DME), diglyme, cyclopentyl methyl ether (CPME), or t-butyl methyl ether (TBME); and aromatic hydrocarbons such as benzene, toluene, xylene, and the like, may be used as solvents. The solvent is preferably selected from ethers, particularly preferably from diethylethers. The reaction is preferably performed in anhydrous condition. The solvents used in the First and Second Steps may be the same or different.

Examples of metal reagents used to exchange a halogen atom (X) of the compound represented by Formula (4) for a metal include lithium reagents and magnesium reagents.

Examples of lithium reagents include metal lithium, alkyl lithium (such as methyllithium, n-butyllithium, sec-butyllithium, or tert-butyllithium), and phenyl lithium. These lithium reagents perform halogen-lithium exchange reaction. n-Butyllithium is preferable.

Examples of magnesium reagents include magnesium metal and alkyl magnesium halide (such as isopropyl magnesium chloride, or isopropyl magnesium bromide). These magnesium reagents perform halogen-magnesium exchange reaction. Isopropyl magnesium chloride is preferable.

The above metal reagent may be a commercially available reagent, or may be easily prepared by a person skilled in the art according to a known method.

The amount of the metal reagent is generally 1 to 1.5 mol, preferably 1 to 1.2 mol, more preferably 1 to 1.15 mol, per mol of the compound represented by Formula (4).

The amount of the compound represented by Formula (5) is generally 0.1 to 0.6 mol, preferably 0.3 to 0.5 mol, more preferably 0.35 to 0.5 mol, particularly preferably 0.4 to 0.5 mol, per mol of the compound represented by Formula (4).

Further, metal salts such as cerium chloride, lithium chloride, magnesium bromide, or copper chloride, may be used together with the metal reagent. This suppresses side reaction or increase solubility of the reagent in organic solvents, thereby promoting the reaction. In particular, such an effect is increased when metal salts are used with a lithium reagent.

The amount of metal salts is generally 0.1 to 100 mol, preferably 0.5 to 20 mol, per mol of the compound represented by Formula (4).

In both the First and Second Steps, the reaction temperature is generally selected from a range of −100° C. to the boiling point of the solvent (e.g., 35° C. when diethylether is used as a solvent). Preferably, when alkyl lithium is used in the First Step, the reaction temperature is preferably about −100° C. to 0° C., more preferably about −80° C. to −40° C. Further, the reaction temperatures in the First and Second Step may be the same or different.

In the First and Second Steps, the reaction is preferably performed in an inactive gas (for example, nitrogen, argon, etc.) atmosphere.

The reaction time is not particularly limited. In both the First and Second Steps, the reaction time is, for example, 1 to 24 hours.

After the reaction, the reaction product can be isolated and purified by subjecting the reaction mixture to a general isolation step such as filtration, concentration, or extraction; and, as necessary, a general purification step such as column chromatography, or recrystallization.

Although the compound represented by Formula (3a) obtained by the above reaction generally has isomers with different configurations, i.e., a cis-isomer (3a-cis) and a trans-isomer (3a-trans), the cis-isomer can be selectively obtained. The cis-isomer can be easily obtained through the above isolation and purification steps. Since the molecules in the cis-isomer (3a-cis) are curved into an L-shape, the cis-isomer efficiently produces a cyclic product by the later-described coupling reaction. For example, in the compound represented by Formula (3a-cis) wherein all k are 0 and all m are 1, the angle created by the two condensed aromatic groups at 1 and 4 positions of the 1,4-dihydro naphthalene ring is about 70°.

The compound represented by Formula (3a) obtained by the above reaction may be directly subjected to the next reaction as a mixture. As necessary, the compound may be subjected to the next reaction after isolation and purification of cis-isomer.

[Chem. 15]

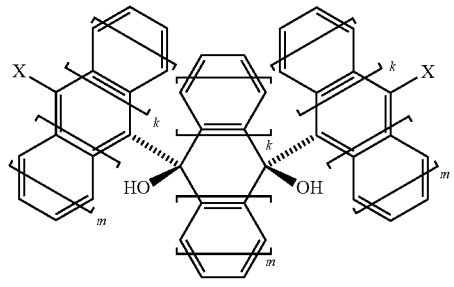

(3a-cis)

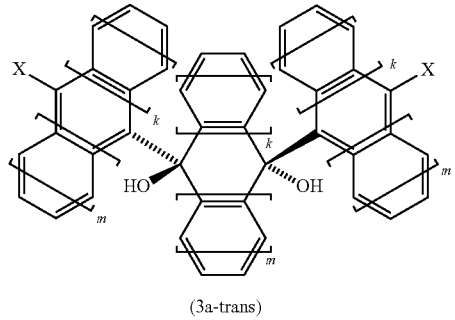

(3a-trans)

wherein X, k and m are as defined above; the solid line shows a position extending out of the paper, and the dotted line shows a position extending into the paper. Note that they show a relative configuration.

Synthesis of Compound (3b)

The compound represented by Formula (3b) can be produced by alkylating the hydroxyl group of the compound represented by Formula (3a) (in particular, the compound represented by Formula (3a-cis)), or by protecting it with a protecting group for a hydroxy group.

Generally, the alkylation reaction may be performed in the presence or absence of a solvent, in the presence of a base, using an alkylating agent.

Examples of solvents include ethers such as diethylether, diisopropyl ether, tetrahydrofuran (THF), 1,4-dioxane, dimethoxyethane (DME), diglyme, cyclopentyl methyl ether (CPME), or t-butyl methyl ether (TBME); aromatic hydrocarbons such as benzene, toluene, or xylene; amides such as dimethyl formamide (DMF), dimethylacetamide (DMA), or N-methylpyrrolidone (NMP); and dimethyl sulfoxides. Among them, ethers are preferable, and tetrahydrofuran is particularly preferable. The reaction is preferably performed in anhydrous conditions.

Examples of bases include alkali metal hydrides such as sodium hydride, calcium hydride, or lithium hydride; alkali metal hydroxides such as sodium hydroxide or potassium hydroxide; alkali metal alkoxides such as sodium methoxide or sodium ethoxide; and nitrogen-containing organic compounds such as triethyl amine, diisopropylethylamine, 1,8-diazabicyclo[5.4.0]undeca-7-ene (DBU), 1,5-diazabicyclo[4.3.0]nonene-5 (DBN), or pyridine. Among them, alkali metal hydrides are preferable, and sodium hydride is particularly preferable.

As the alkylating agent, generally, $C_{1-6}$ alkylating agents are preferably used. Examples thereof include alkyl halides (such as methyl iodide or ethyl iodide), dialkyl sulfates (such as dimethyl sulfate or diethyl sulfate), alkyl triflate, and alkyl tosylate. Among them, alkyl halides are preferable, and methyl iodide is particularly preferable.

The amount of the base is generally about 2 to 50 mol, preferably about 2 to 30 mol, more preferably about 2 to 15 mol, per mol of the compound represented by Formula (3a).

The amount of the alkylating agent is generally about 2 to 50 mol, preferably about 2 to 30 mol, more preferably about 2 to 15 mol, per mol of the compound represented by Formula (3a).

Generally, the reaction temperature is suitably selected from the range of −50° C. to the boiling point of the solvent. The reaction temperature is preferably selected from the range of −10° C. to the boiling point of the solvent.

The reaction is preferably performed in an inactive gas (for example, nitrogen, argon, etc.) atmosphere.

The reaction time is not particularly limited; for example, the reaction time is 1 minute to 100 hours.

The reaction by the protection with a protecting group for a hydroxy group may also be performed by using hitherto-known protection reactions that enable introduction of a protecting group for a hydroxy group (such as alkanoyl group, substituted or unsubstituted aralkyl group, silyl group, alkoxy alkyl group, or tetrahydropyranyl group).

After the reaction, the reaction product can be isolated and purified by subjecting the reaction mixture to a general isolation step such as filtration, concentration, or extraction; and, as necessary, a general purification step such as column chromatography, or recrystallization.

The compound represented by Formula (3b) obtained by the above reaction generally has isomers with different configurations, i.e., a cis-isomer (3b-cis) and a trans-isomer (3b-trans) when the compound represented by Formula (3a) is a mixture of cis-isomers and trans-isomers. However, cis-isomer can be selectively obtained by the above isolation means.

Figure 2:
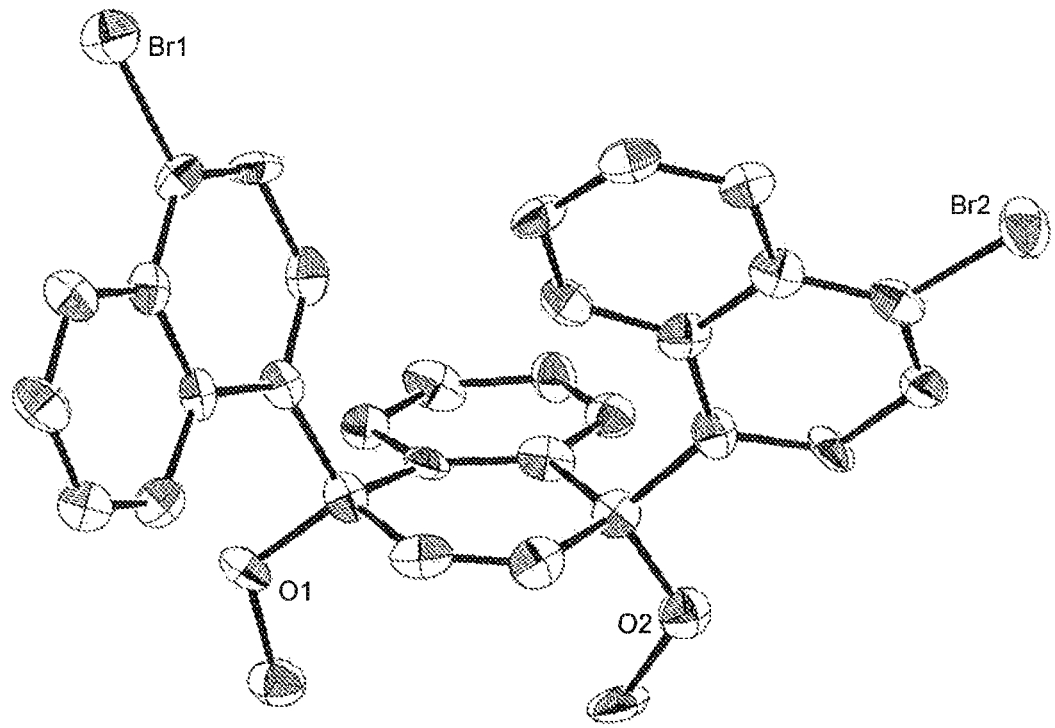
FIG. 2 shows an X-ray crystal-structure analysis (Oak Ridge Thermal Ellipsoid Plot) of a compound obtained in Example 2.

Table 1 and FIG. 2 show X-ray crystallography of the compound obtained in Example 2, which is an example of a cis-isomer (3b-cis) obtained by the above reaction.

The compound represented by Formula (3a) and the compound represented by Formula (3b) may be collectively represented as the compound represented by Formula (3). The compound represented by Formula (3) may be subjected to the following reaction.

[Chem. 16]

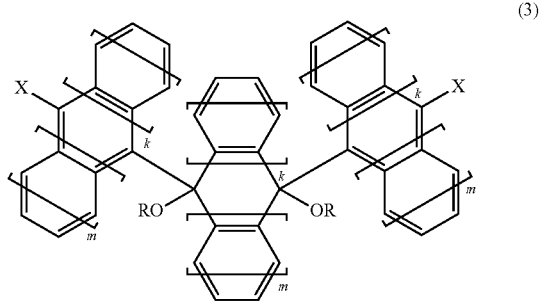

wherein R, X, k and m are as defined above.

Synthesis of Compound (2)

Generally, the compound represented by Formula (2) can be produced by reacting (homocoupling reaction) the compound represented by Formula (3) (preferably the compound represented by Formula (3b-cis)) in the presence of a solvent and a transition metal compound.

Examples of transition metal compound include compounds containing the transition metals in Group 10 (Ni, Pd, Pt), preferably compounds containing nickel (Ni). Preferable examples of the compounds containing nickel (Ni) include compounds (salts or complexes) of zerovalent Ni(0) or bivalent Ni(II). They may be used singly, or in a combination of two or more.

Examples of Ni(0) compounds include bis(1,5-cyclo-octadiene)nickel(0) (Ni(cod)$_2$), bis(triphenylphosphine) nickeldicarbonyl and nickelcarbonyl.

Further, examples of Ni(II) compounds include nickel(II) acetate, nickel(II)trifluoroacetate, nickel(II)nitrate, nickel(II)chloride, nickel(II)bromide, nickel(II)acetylacetonato, nickel(II)perchlorate, nickel(II)citrate, nickel(II)oxalate, nickel cyclohexanebutyrate, nickel(II)benzoate, nickel(II) stearate, nickel(II) stearate, nickel(II)sulfamate, nickel(II) carbonate, nickel(II)thiocyanate, nickel(II)trifluoromethanesulfonate, bis(1,5-cyclo-octadiene)nickel(II), bis(4-diethylamino dithiobenzyl)nickel (II), nickel(II) cyanide, nickel fluoride (II), nickel(II)boride, nickel(II)borate, nickel (II)hypophosphite, ammonium nickel(II)sulfate, nickel(II) hydroxide, nickel(II)cyclopentadienyl, hydrates thereof, and mixtures thereof.

The zerovalent Ni(0) compounds and bivalent Ni(II) compounds are preferably zerovalent Ni(0) compounds, particularly preferably bis(1,5-cyclo-octadiene)nickel(0).

Examples of zerovalent Ni(0) compounds and bivalent Ni(II) compounds also include compounds with previously coordinated ligands.

The amount of the transition metal compound is generally 0.01 to 50 mol, preferably 0.1 to 10 mol, more preferably 0.5 to 5 mol, and particularly preferably 1 to 3 mol, per mol of Compound (3) used as a raw material.

In this reaction, in addition to the transition metal compounds, it is possible to use ligands that can be coordinated to transition metals (nickel (nickel atom) etc.) that constitute the transition metal compounds. Examples of such ligands include carboxylate-based ligands, amide-based ligands, phosphine-based ligands, oxime-based ligands, sulfonate-based ligands, 1,3-diketone-based ligands, Schiff base ligands, oxazoline-based ligands, diamine-based ligands, carbon monoxide ligands, carbene-based ligands, and the like. They may be used singly, or in a combination of two or more. The coordinating atoms in the ligands are a nitrogen atom, phosphorus atom, oxygen atom, sulfur atom, and the like. These ligands include monodentate ligands having a coordinating atom at one site, and multidentate ligands having coordinating atoms at two or more sites. Further, in carbon monoxide ligands and carbene-based ligands, carbon atoms serve as coordinating atoms.

Examples of monodentate ligands include triphenylphosphine, trimethoxyphosphine, triethylphosphine, tri(i-propyl)phosphine, tri(tert-butyl)phosphine, tri(n-butyl)phosphine, tri(isopropoxy)phosphine, tri(cyclopentyl)phosphine, tri(cyclohexyl)phosphine, tri(ortho-toluoyl)phosphine, tri(mesityl)phosphine, tri(phenoxy)phosphine, tri-(2-furyl)phosphine, bis(p-sulfonatophenyl)phenylphosphine potassium, di(tert-butyl)methylphosphine, methyldiphenylphosphine, dimethylphenylphosphine, triethylamine, pyridine, and the like.

Examples of bidentate ligands include 2,2'-bipyridyl, 4,4'-(tert-butyl)bipyridyl, phenanthroline, 2,2'-bipyrimidyl, 1,4-diazabicyclo[2,2,2]octane, 2-(dimethylamino)ethanol, tetramethylethylenediamine, N,N-dimethylethylenediamine, N,N'-dimethylethylenediamine, 2-aminomethylpyridine, or (NE)-N-(pyridine-2-ylmethyliden)aniline, 1,1'-bis(diphenylphosphino)ferrocene, 1,1'-bis(tert-butyl)ferrocene, diphenylphosphino methane, 1,2-bis(diphenylphosphino)ethane, 1,3-bis(diphenylphosphino)propane, 1,5-bis(diphenylphosphino)pentane, 1,2-bis(dipentafluorophenylphosphino)ethane, 1,2-bis(dicyclohexylphosphino)ethane, 1,3-(dicyclohexylphosphino)propane, 1,2-bis(di-tert-butylphosphino)ethane, 1,3-bis(di-tert-butylphosphino)propane, 1,2-bis(diphenylphosphino)benzene, 1,5-cyclooctadiene, 2,2'-bis(diphenylphosphino)-1,1'-binaphthyl (BINAP), 2,2'-dimethyl-6,6'-bis(diphenylphosphino)biphenyl (BIPHEMP), 1,2-bis(diphenylphosphino)propane (PROPHOS), 2,3-O-isopropylidene-2,3-dihydroxy-1,4-bis(diphenylphosphino)butane (DIOP), 3,4-bis(diphenylphosphino)-1-benzylpyrrolidine (DEGUPHOS), 1,2-bis [(2-methoxyphenyl)phenylphosphino]ethane (DIPAMP), substituted-1,2-bis-(phospholano)benzene (DuPHOS), 5,6-bis-(diphenylphosphino)-2-norbornene (NORPHOS), N,N'-bis(diphenylphosphino)-N,N'-bis(1-phenylethyl)ethylene diamine (PNNP), 2,4-bis(diphenylphosphino)pentane (SKEWPHOS), 1-[1',2-bis(diphenylphosphino)ferrocenyl] ethylene diamine (BPPFA), 2,2'-bis(dicyclohexylphosphino)-5,5',6,6',7,7',8,8'-octahydro-1,1'-binaphthyl, ((4,4'-bi-1,3-benzodioxole)-5,5'-diyl)bis(diphenylphosphine) (SEGPHOS), 2,3-bis(diphenylphosphino)butane (CHIRAPHOS), 1-[2-(2-substituted-phosphino)ferrocenyl]ethyl-2-substituted-phosphine (JOSIPHOS), and mixtures thereof.

Further, examples of BINAP include BINAP(2,2'-bis(diphenylphosphino)-1,1'-binaphthyl) derivatives. Examples thereof include 2,2'-bis(diphenylphosphino)-1,1'-binaphthyl, 2,2'-bis(di-p-tolylphosphino)-1,1'-binaphthyl, 2,2'-bis(di-p-tertiary-butylphenylphosphino)-1,1'-binaphthyl, 2,2'-bis(di-m-tolylphosphino)-1,1'-binaphthyl, 2,2'-bis(di-3,5-dimethylphenylphosphino)-1,1'-binaphthyl, 2,2'-bis(di-p-methoxyphenylphosphino)-1,1'-binaphthyl, 2,2'-bis(dicyclopentylphosphino)-1,1'-binaphthyl, 2,2'-bis(dicyclohexylphosphino)-1,1'-binaphthyl, 2-di(β-naphthyl)phosphino-2'-diphenylphosphino-1,1'-binaphthyl, 2-diphenylphosphino-2'-di(p-trifluoromethylphenyl)phosphino-1,1'-binaphthyl, and the like.

Further, examples of BIPHEMP include BIPHEMP(2,2'-dimethyl-6,6'-bis(diphenylphosphino)biphenyl) derivatives. Examples thereof include 2,2'-dimethyl-6,6'-bis(diphenylphosphino-1,1'-biphenyl, 2,2'-dimethyl-6,6'-bis(dicyclohexylphosphino)-1,1'-biphenyl, 2,2'-dimethyl-4,4'-bis(dimethylamino)-6,6'-bis(diphenylphosphino)-1,1'-biphenyl, 2,2',4,4'-tetramethyl-6,6'-bis(diphenylphosphino)-1,1'-biphenyl, 2,2'-dimethoxy-6,6'-bis(diphenylphosphino)-1,1'-biphenyl, 2,2',3,3'-tetramethoxy-6,6'-bis(diphenylphosphino)-1,1'-biphenyl, 2,2',4,4'-tetramethyl-3,3'-dimethoxy-6,6'-bis(diphenylphosphino)-1,1'-biphenyl, 2,2'-dimethyl-6,6'-bis(di-p-tolylphosphino)-1,1'-biphenyl, 2,2'-dimethyl-6,6'-bis(di-p-tert-butylphenylphosphino)-1,1'-biphenyl, and 2,2',4,4'-tetramethyl-3,3'-dimethoxy-6,6'-bis(di-p-methoxyphenylphosphino)-1,1'-biphenyl.

Among these ligands, 2,2'-bipyridyl is preferable.

When these ligands are used, the amount thereof is generally 0.01 to 50 mol, preferably 0.1 to 10 mol, more preferably 0.5 to 5 mol, and particularly preferably 1 to 3 mol, per mol of Compound (3) used as a raw material.

Examples of reaction solvents to be used in this reaction include aliphatic hydrocarbons such as hexane, cyclohexane, or heptane; aliphatic halogenated hydrocarbons such as dichloromethane, chloroform, carbon tetrachloride, or dichloroethane; aromatic hydrocarbons such as benzene, toluene, xylene, or chlorobenzene; ethers such as diethylether, diisopropylether, dibutylether, dimethoxyethane (DME), cyclopentylmethylether (CPME), tert-butylmethylether, tetrahydrofuran (THF), or dioxane; esters such as ethyl acetate, or ethyl propanoate; amides such as dimethylformamide (DMF), dimethylacetamido (DMA), or N-methylpyrrolidone (1-methyl-2-pyrrolidone) (NMP); nitriles such as acetonitrile, or propionitrile; and dimethylsulfoxides (DMSO). They may be used singly, or in a combination of two or more. Ethers or amides are preferable, and tetrahydrofuran or dimethyl formamide is particularly preferable. The reaction is preferably performed in anhydrous condition.

The amount of the solvent is generally 1 to 1000 parts by mass, preferably 5 to 200 parts by mass, and more preferably 10 to 100 parts by mass, per 100 parts by mass of the compound represented by Formula (3).

The reaction temperature is generally not less than 0° C. and not more than the boiling point of the reaction solvent.

The reaction atmosphere is not particularly limited; however, an inert gas atmosphere, such as an argon gas atmosphere or a nitrogen gas atmosphere, is preferable. An air atmosphere may also be adopted.

After the reaction, the reaction product can be isolated by subjecting the reaction mixture to a general isolation step such as filtration, concentration, or extraction; and, as necessary, to a general purification step such as column chromatography or recrystallization.

In this reaction, since the compound represented by Formula (3) has an L-shape, the halogen atoms (X) serving as the reaction sites in the individual molecules more easily approach each other, and the homocoupling reaction is efficiently advanced, thereby easily obtaining a cyclic compound. Thereby, this reaction produces a trimer, a tetramer, a pentamer, etc., of the compound represented by Formula (3). They correspond to a cyclic compound represented by Formula (2) wherein n=3, 4, and 5, respectively.

Synthesis of Compound (1)

The compound represented by Formula (1) (cyclopolyarylene compound) is generally produced by reducing (more specifically, through reductive aromatization) the compound represented by Formula (2) in the presence of a solvent and a reducing agent.

Examples of usable solvents include ethers such as diethyl ether, diisopropyl ether, tetrahydrofuran (THF), 1,4-dioxane, dimethoxyethane (DME), diglyme, cyclopentylmethylether (CPME), or t-butyl methyl ether (TBME); and aromatic hydrocarbons such as benzene, toluene, or xylene. Ethers are preferable, and tetrahydrofuran is particularly preferable. The reaction is preferably performed in anhydrous condition.

Examples of reducing agents include metallic lithium, metallic sodium, metallic potassium, metallic magnesium, and tin chloride (II). Metallic lithium is preferable.

The amount of the reducing agent is generally 1 to 500 mol, preferably 5 to 300 mol, per mol of the compound represented by Formula (2).

The reaction temperature is generally selected from a range of not less than 0° C. and not more than the boiling point of the reaction solvent.

The reaction atmosphere is not particularly limited; however, an inert gas atmosphere, such as an argon gas atmosphere or a nitrogen gas atmosphere, is preferable. An air atmosphere may also be adopted.

After the reaction, the reaction product can be isolated by subjecting the reaction mixture to a general isolation step such as filtration, concentration, or extraction; and, as necessary, a general purification step such as column chromatography or recrystallization.

The compound represented by Formula (1) is a ring wherein n is 3, 4, 5 or 6. However, when n is an odd number, the compound has axial chirality.

The production method of the present invention enables simple production of the cyclopolyarylene compound represented by Formula (1) (wherein n is 3, 4, 5 or 6).

EXAMPLES

Hereinafter, the present invention is described in further detail with reference to Examples. However, the scope of the invention is not limited to these Examples. NMR measurements in the Examples were performed using a nuclear magnetic resonance spectrometer (model name: A-400) produced by JEOL Ltd.

Example 1

Synthesis of Compound 1

[Chem. 17]

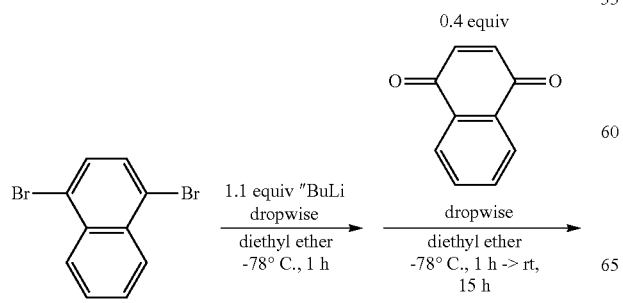

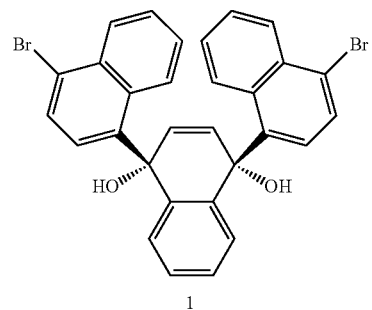

A 500-mL three-necked round bottom flask containing a stirring bar was dried by heating under reduced pressure. After the flask was cooled to room temperature, argon was introduced thereinto. A solution (21.0 mL, 29.4 mmol) of 1.4 M n-butyllithium in hexane was slowly added at −78° C. to a solution of 1,4-dibromonaphthalene (7.51 g, 26.3 mmol) in dry diethyl ether (345 mL). The reaction mixture was stirred at −78° C. for 1 hour. A solution of 1,4-naphthoquinone (1.66 g, 10.5 mmol) in dry diethyl ether (100 mL) was then added thereto, and the mixture was stirred at −78° C. for 1 hour and at room temperature for 15 hours. The reaction mixture was quenched with water, extracted with EtOAc (100 mL×3), dried over $Na_2SO_4$, and then concentrated under reduced pressure. The crude product was purified by silica gel column chromatography ($CHCl_3$/EtOAc=20/1) and reprecipitation (THF/hexane) to thereby yield Compound 1 as a white solid (1.28 g, 21%). It was possible to improve the yield to 36% by adjusting the amounts of the solvents and the reaction time.

Compound 1:
$^1$H NMR (400 MHz, $CDCl_3$) δ 3.52 (br, 2H), 6.58 (s, 2H), 6.84 (br, 2H), 7.05 (s, 2H), 7.42 (dd, J=7 Hz, 2H), 7.58 (dd, J=8 Hz, 2H), 7.68 (br, 2H), 7.98 (d, J=8 Hz, 2H), 8.09 (br, 2H), 8.39 (d, J=8 Hz, 2H).

Example 2

Synthesis of Compound 2 (Methylation Reaction)

[Chem. 18]

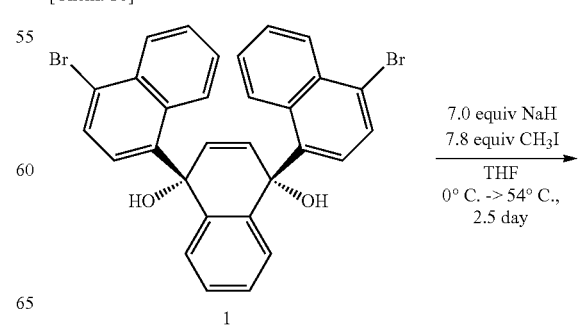

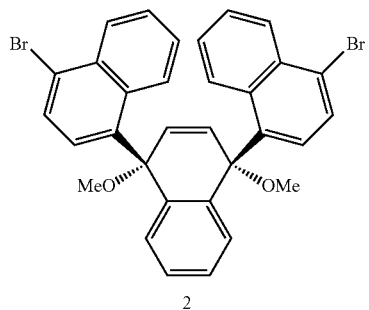

2

A 200-mL two-necked round bottom flask containing a stirring bar was dried by heating under reduced pressure. After the flask was cooled to room temperature, argon was introduced into the flask. A solution of Compound 1 (200 mg, 350 μmol) in dry THF (3.5 mL) was slowly added at 0° C. to a mixture of sodium hydride (60% oily suspended substance, 108 mg, 2.45 mmol) and dry THF (6 mL). Methyl iodide (170 μL, 2.73 mmol) was added at 0° C. dropwise to the resulting reaction mixture and stirred at 54° C. for 2.5 days. The reaction mixture was quenched with water and extracted with EtOAc (30 mL×3). The combined organic layers were dried over $Na_2SO_4$ and concentrated under reduced pressure. The crude product was purified by reprecipitation (THF/hexane) to yield Compound 2 as a white solid (200 mg, 96%).

Compound 2:

$^1$H NMR (400 MHz, $CDCl_3$) δ 3.35 (s, 6H), 6.73 (s, 2H), 6.93 (d, J=8 Hz, 2H), 7.46 (dd, J=3 Hz, J=6 Hz, 2H), 7.56 (d, J=8 Hz, 2H), 7.62 (dd, J=3 Hz, J=6 Hz, 2H) 8.28 (dd, J=1 Hz, J=8 Hz, 2H), 8.85 (d, J=9 Hz, 2H).

Table 1 shows the results of the X-ray crystal structure analysis of Compound 2. FIG. 2 is an ORTEP drawing.

TABLE 1

| | Compound 2 |
|---|---|
| Formula | $C_{32}H_{24}Br_2O_2$ |
| Fw | 600.33 |
| T (K) | 123(2) |
| λ (Å) | 0.7107 |
| cryst syst | Monoclinic |
| space group | $P2_1/a$ |
| a, (Å) | 7.643(3) |
| b, (Å) | 25.951(10) |
| c, (Å) | 13.133(6) |
| α, (deg) | 90 |
| β, (deg) | 104.331(8) |
| γ, (deg) | 90 |
| V, (Å$^3$) | 2523.9(18) |
| Z | 4 |
| $D_{calc}$, (g/cm$^3$) | 1.580 |
| μ (mm$^{-1}$) | 3.241 |
| F(000) | 1208 |
| cryst size (mm) | 0.10 × 0.02 × 0.01 |
| 2θ range, (deg) | 3.14-25.00 |
| reflns collected | 16872 |
| indep reflns/$R_{int}$ | 4430/0.1150 |
| Params | 327 |
| GOF on F$^2$ | 1.044 |
| $R_1$, w$R_2$ [I > 2 σ (I)] | 0.0876, 0.1990 |
| $R_1$, w$R_2$ (all data) | 0.1472, 0.2451 |

Example 3

Synthesis of Compound 3 (Homocoupling Reaction)

[Chem. 19]

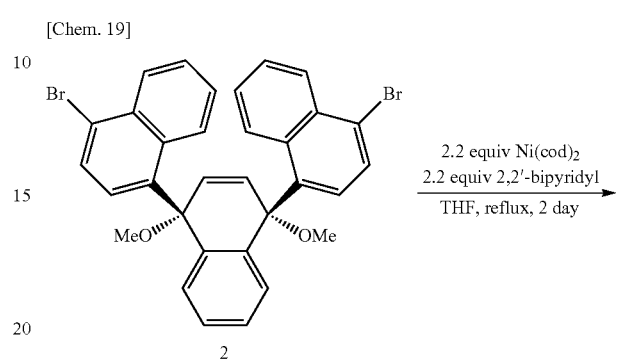

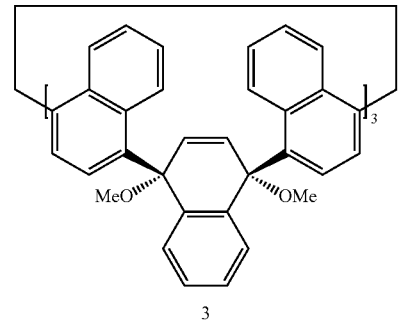

A Schlenk flask containing a stirring bar was dried by heating under reduced pressure. After the flask was cooled to room temperature, argon was introduced into the flask. Compound 2 (50.0 mg, 83.3 μmol), Ni(cod)$_2$ (50.8 mg, 183 μmol), 2,2'-bipyridyl (29.2 mg, 194 mol), and dry THF (3 mL) were added to the Schlenk flask in a glovebox. The mixture was stirred at reflux under pressure for 2 hours. Water was added to the reaction mixture, and extracted with $CH_2Cl_2$ (10 mL×3). The organic layers were combined and subjected to preparative recycling gel permeation chromatography ($CHCl_3$), and then purified by PTLC ($CH_2Cl_2$/hexane=4/1) to thereby yield Compound 3 as a white solid (4.8 mg, 3.3%). When the same reaction was performed as above using Compound 2 (100 mg, 166 μmol), Ni(cod)$_2$ (101 mg, 367 μmol), 2,2'-bipyridyl (57.2 mg, 366 μmol), and dry DMF (20 mL), under increased pressure at 85° C. for 39 hours, instead of at reflux for 2 hours, Compound 3 (3.8 mg, 2%) was obtained in a similar manner to the above.

Compound 3:

$^1$H NMR (600 MHz, $CDCl_3$) δ 3.35 (s, 4H) 3.38 (s, 4H), 3.39 (s, 4H), 3.43 (s, 4H), 3.44 (s, 4H), 3.47 (s, 4H), 6.58 (d, J=10 Hz, 1H), 6.75 (d, J=7 Hz, 1H), 6.82 (d, J=7 Hz, 1H), 6.85 (d, J=11 Hz, 1H), 6.95-7.83 (m, <60H), 8.08 (d, J=8 Hz, 1H), 8.63 (d, J=8 Hz, 1H), 9.06 (d, J=9 Hz, 1H), 9.10 (d, J=9 Hz, 1H), 9.16 (t, J=8 Hz, 2H), 9.68 (d, J=9 Hz, 1H); LRMS (FAB-MS) m/z calcd. for $C_{96}H_{72}O_6$ [M]$^+$: 1320.53. found: 1320.

Example 4

Synthesis of Compound [9]Cyclonaphthylene ([9]CN) (Reductive Aromatization Reaction)

[Chem. 20]

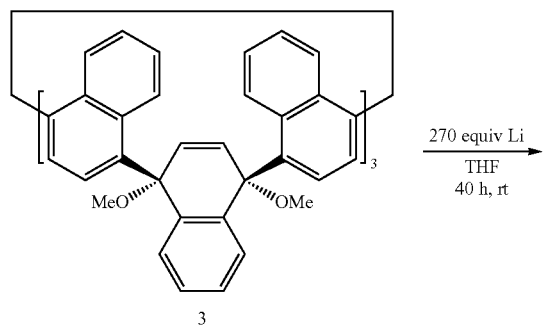

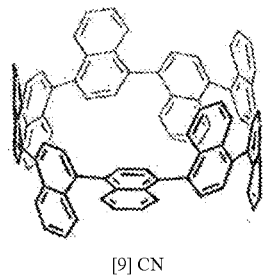

[9] CN

A 30-ml vial containing a stirring bar covered with glass was dried by heating under reduced pressure. After the vial was cooled to room temperature, argon was introduced thereinto. Compound 3 (4.8 mg, 3.7 μmol), granular lithium (7.2 mg, 1.0 mmol), and Dry THF (2 mL) were added thereto in a glovebox, and the mixture was stirred at room temperature for 40 hours. The reaction mixture was diluted with hexane and quenched with methanol. After the solvent was distilled off, the reaction mixture was passed through a short silica gel pad (CHCl$_3$). The filtrate was concentrated, followed by purification by PTLC (CH$_2$Cl$_2$/hexane=1/1), to yield Compound [9]cyclonaphthylene ([9]CN) as a yellow solid (0.6 mg, 15%). It was possible to improve the yield to 59% by repeatedly isolating Compound (3) and adjusting the amount of granular lithium, before performing Example 4.

Compound [9]CN:

$^1$H NMR (600 MHz, CDCl$_3$) δ 6.33 (s, 2H), 7.01 (d, J=5 Hz, 8H), 7.16 (d, J=8 Hz, 2H), 7.20 (d, J=7 Hz, 2H), 7.24 (s, 1H), 7.34 (t, J=8 Hz, 2H), 7.42 (d, J=8 Hz, 2H), 7.48 (t, J=8 Hz, 2H), 7.59 (d, J=10 Hz, 5H), 7.75 (d, J=10 Hz, 2H), 8.33 (dd, J=4 Hz, J=6 Hz, 2H) 8.45 (d, J=4 Hz, 2H), 8.50 (dd, J=4 Hz, J=6 Hz, 2H), 8.54 (dd, J=4 Hz, J=6 Hz, 2H), 8.58 (d, J=10 Hz, 3H), 8.61 (d, J=7 Hz, 3H) 8.78 (d, J=8 Hz, 2H); HRMS (MALDI TOF-MS) m/z calcd. for C$_{90}$H$_{54}$ [M]$^+$ 1134.42. found: 1134.27.

The invention claimed is:

1. A cyclopolyarylene compound corresponding to Formula (1):

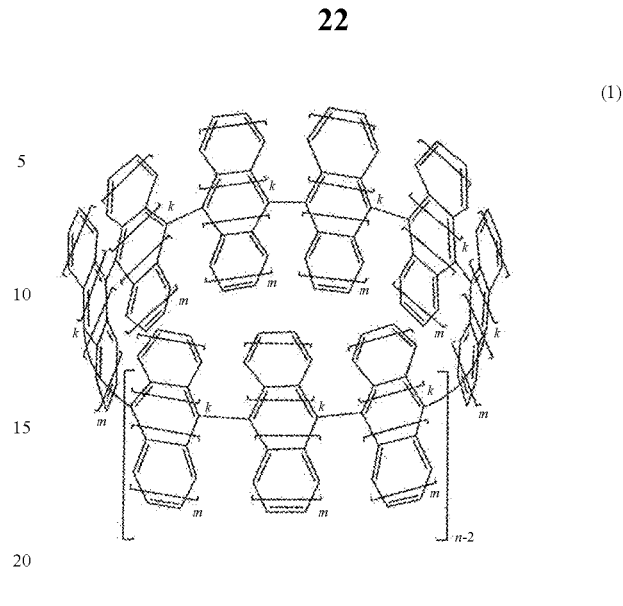

wherein k is the same or different, and each corresponds to 0, 1 or 2; m is the same or different, and each corresponds to 1, 2 or 3; and n is 3, 4, 5 or 6.

2. The cyclopolyarylene compound according to claim 1, wherein all k are the same; and all m are the same in Formula (1).

3. The cyclopolyarylene compound according to claim 1, wherein all k are 0 or 1; all m are 1 or 2; and n is 3 or 4 in Formula (1).

4. A method for producing a cyclopolyarylene compound according to claim 1, the method comprising the step of aromatizing a compound corresponding to Formula (2):

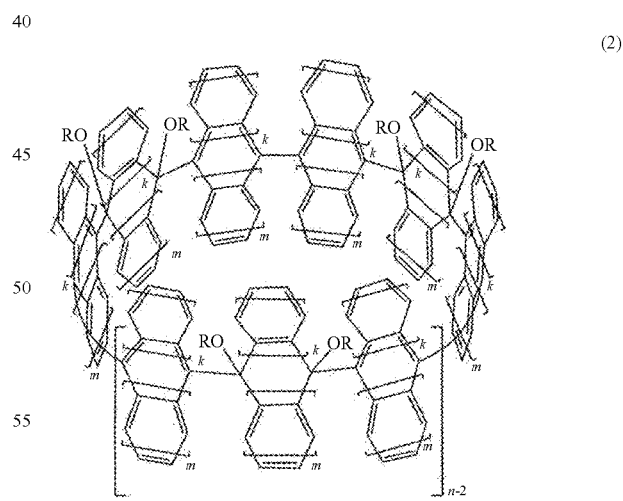

wherein R is the same or different, and each corresponds to hydrogen atom, alkyl group or protecting group for hydroxy group; and k, m and n are as defined above.

5. The method according to claim 4, comprising the step of reacting a compound corresponding to Formula (3):

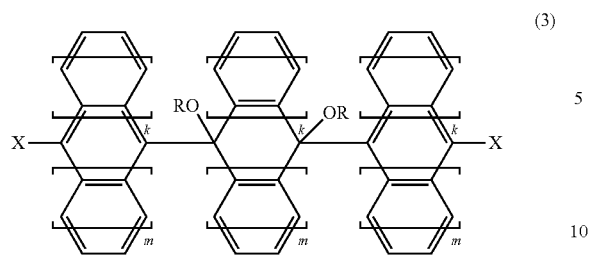 (3)
wherein X is the same or different, and each corresponds to halogen atom; and R, k and m are as defined above, in the presence of a transition metal compound, thereby obtaining the compound corresponding to Formula (2).
* * * * *